United States Patent [19]

Reysis

[11] Patent Number: 5,549,930
[45] Date of Patent: Aug. 27, 1996

[54] DRYER AND TOP COAT FOR NAIL POLISH

[76] Inventor: Moisei Reysis, 37140 Independence Ct., Solon, Ohio 44139

[21] Appl. No.: 450,527

[22] Filed: May 25, 1995

[51] Int. Cl.$^6$ .............................. B05D 3/02; B05D 3/04; B05D 3/10
[52] U.S. Cl. .............................. 427/337; 424/61; 427/389
[58] Field of Search ................................. 427/389, 407.1, 427/337; 424/61

[56] References Cited

U.S. PATENT DOCUMENTS

| | | | |
|---|---|---|---|
| 4,530,726 | 7/1985 | Montiel | 134/38 X |
| 5,194,292 | 3/1993 | Billings | 427/389 X |
| 5,336,692 | 8/1994 | Gans et al | 514/772 |

Primary Examiner—Michael Lusignan
Attorney, Agent, or Firm—Fay, Sharpe, Beall, Fagan, Minnich & McKee

[57] ABSTRACT

The present invention is directed to a silicon based drying accelerator and top coat for wet nail polish, as well as a method for drying nail polish using the accelerator. The silicone based composition is comprised of at least 50% dimethicone and at least 25% cyclomethicone. It may be applied to wet nail polish using traditional spray or brush methods, or by using a dropper. The drying accelerator significantly reduces nail polish drying time over natural and other drying methods. The composition poses no health or environmental detriment.

10 Claims, No Drawings

DRYER AND TOP COAT FOR NAIL POLISH

BACKGROUND OF THE INVENTION

The present invention is directed to a combination drying and top coat agent for use in association with the application of nail polish.

Top coats of the prior art contain solvents and diluents which pose health and environmental concerns. Some of these undesirable components present in prior art top coats include butyl acetate, ethyl acetate, alcohols, toluene, formaldehyde and others. In addition, compounds which are marketed as fast or quick dry top coats typically require at least 5–7 minutes for two coats of underlying nail polish to be dry to the touch, and require even longer durations for the nail polish to dry throughout.

Furthermore, many of the prior art products require devices such as heating lamps and UV light for curing the resins in the top coat. Such devices are only useful for applications on artificial nails. Use in applications on natural nails leads to undesirable results such as peeling of nail polish.

The present invention is directed to a solvent-free dryer and top coat for nail polish application.

BRIEF DESCRIPTION OF THE INVENTION

In accordance with the present invention, there is provided a composition and method for simultaneously drying nail polish and applying a top coat to nail polish.

In accordance with a more limited aspect of the invention, a drying accelerator for nail polish consists essentially of at least 50% dimethicone and at least 25% cyclomethicone. Wet nail polish may be dried by applying drops of the drying accelerator to wet nail polish using a dropper. The drying accelerator serves to extract solvents from the wet nail polish so that the polish dries. A top coat then remains over the nail polish.

A principle advantage of the invention is that the drying and top coat composition is solvent free. As a result, health and environmental risks are alleviated. Also, this aspect provides for the ability to apply the nail polish using a pipette or dropper.

Another advantage of the present invention is that the duration required for drying nail polish is decreased in comparison to drying compositions of the prior art. Where it once took 5–7 minutes to dry nail polish to the touch, the present application dries 2 coats of nail polish to the touch in roughly 3 minutes, and roughly 5 minutes for total and complete curing.

Another advantage of the present invention is that no devices are required to dry the nail polish. No UV lights are required and no heat lamps are required. As a result, the composition may be applied universally to both natural and artificial nails. Artificial nails, not natural nails, may be dried by UV and heat lamp methods.

Yet another advantage of the present invention is found in the economy of production. The product comprises only two silicon based components—cyclomethicone and dimethicone—in predetermined ratios, without the need for additional constituents.

Still other advantages and benefits of the present invention will become apparent to those skilled in the art upon a reading and understanding of the following detailed description.

DETAILED DESCRIPTION OF THE PREFERRED EMBODIMENT

The present invention is directed to a drying accelerator for nail polish and similar products. The drying accelerator product also provides a top coat over nail polish, leaving a shine. The quick dry composition is a silicon based composition free of solvents.

The product of the present invention is comprised of two silicon based compounds, namely dimethicone and cyclomethicone. The composition calls for about 50%–75% by volume dimethicone, and about 25% to 50% by volume cyclomethicone. The resulting composition is applied to wet fingernail polish. The drying accelerator works to absorb solvents from the nail polish or similar products so that they are expediently evaporated. A dry glossy finish or top coat remains over the nail polish.

The product is applied according to a novel dropper method, although it may likewise be applied by more conventional means such as by brush or sprayer. Because the quick dry product of the present invention contains no solvents or diluents, the dropper provides ease and expediency of application. Use of a dropper with prior art top coats leaves a dip or crater in nail polish. The solvents and diluents present in the prior art top coats dilute the nail polish, and when they are applied by dropper, the diluents begin working immediately on the area where the drop lands, causing the dip or crater. The prior art top coats must be spread by brush or sprayer over the nail in order to maintain a smooth finish. The present invention alleviates the need for manual spreading, and thus a dropper may be used.

Dimethicone is a colorless silicone oil consisting of dimethylsiloxane polymers. It ranges in viscosity from 0.65 to 1 million centistokes at room temperature. Viscosity grades higher than 50 centistokes are immiscible in water and miscible with chloroform and ether. Dimethicone is frequently useful as a component in ointments, topical drugs and skin protectants. Its chemical formula is $CH_3[Si(CH_3)_2O]Si(CH_3)_3$.

Cyclomethicone is a volatile dimethylpolysiloxane compound which has the physical appearance of a fluid of low viscosity (on the order of 2.5 to 6 $mm^2/s$ at 25° C.) with a surface tension on the order of 18–21 mN/m (likewise at about 25° C.). The chemical formula of cyclomethicone is $[Si(CH_3)_2O]_n$, wherein n is a natural integer between 3 and 6.

Dimethicone may be further described as polydimethyl siloxane, with a molecular weight ranging from about 500 to about 26,000. Cyclomethicone may be described as the cyclic tetramer of dimethyl siloxane with a molecular weight of about 296, or the cyclic pentamer of dimethylsiloxane having a molecular weight of about 370. The dimethicone and cyclomethicone silicone fluids just described are supplied by various manufacturers including Dow Corning, General Electric, SWS and Union Carbide under various trade names. They are suitable for human topical application.

The drying composition of the present invention is nontoxic, solvent free and odorless. It poses no environmental or health concerns. The composition comprises an all silicon based composition.

Other products available in the fast drying top coat area may be dried by a variety of ways including natural evaporation, or by using devices such as a UV light for curing UV activated resins or polymers in the polish. Other types of polishes need to be activated by the heat emanating from a heat lamp. Heat lamps and UV lights are only applicable to artificial nails. They cannot be used to dry nail polish applied to natural nails because the polish would peel and shrink as a result of using these methods. The drying accelerator of the present invention may be applied to both natural and artificial nails. Moreover, all of the prior drying methods, including drying by evaporation, cause the emissions of unpleasant odors. No unpleasant odors are emitted using the drying accelerator of the present invention.

EXAMPLE

A drying accelerator/top coat composition comprising dimethicone and cyclomethicone was prepared by mixing two silicon based components, dimethicone and cyclomethicone. The dryer/top coat had the following composition:

Dimethicone - 65%

Cyclomethicone - 35%

Dimethicone and cyclomethicone were combined and mixed at room temperature, and then applied to wet nail polish using a medicine dropper. It was determined that the nail polish was dry to the touch in about 3 minutes and dried all the way through in about 5 minutes. This showed an improvement over the prior art top coats when dry to the touch in around 5–7 minutes.

The composition of the drying accelerator/top coat is not limited to the above composition. It is fully within the scope of this invention that the amount of dimethicone present may be at least 50% and the cyclomethicone may be at least 25% of the overall composition.

The invention has been described with reference to the preferred embodiment. Obviously, modifications and alterations will occur to others upon a reading and understanding of this specification. It is intended to include all such modifications and alterations insofar as they come within the scope of the amended claims or the equivalent thereof.

I claim:

1. A method for drying nail polish, comprising the steps of:

applying at least one layer of nail polish to a nail;

providing a solvent free silicon based drying accelerator;

applying drops of the drying accelerator to wet nail polish using a dropper;

extracting solvents from the wet nail polish via the drying accelerator;

drying the wet nail polish in ambient conditions; and leaving a top coat over the nail polish.

2. A method for drying nail polish, as set forth in claim 1, wherein the solvent free silicon based drying accelerator comprises at least 50% dimethicone and at least 25% cyclomethicone.

3. A method for drying nail polish, as set forth in claim 2, wherein the solvent free silicon based drying accelerator comprises 50%–75% dimethicone and 25%–50% cyclomethicone.

4. A method for drying nail polish, as set forth in claim 1, wherein the drying accelerator consists essentially of cyclomethicone and dimethicone.

5. A method for drying nail polish, comprising the steps of:

applying wet nail polish to a nail;

dropping drops of a drying accelerator comprising at least 25% cyclomethicone and 50% dimethicone on the wet nail polish;

extracting nail polish solvents via the drying accelerator to accelerate the drying time of the wet nail polish; and drying the nail polish.

6. The method of claim 5 wherein the step of drying the nail polish occurs without a need for a light or heat source.

7. The method of claim 5 wherein the drying accelerator consists essentially of cyclomethicone and dimethicone.

8. The method of claim 5 wherein the drying accelerator comprises 50–75% dimethicone and 25–50% cyclomethicone.

9. A method for drying nail polish, comprising the steps of:

coating a nail with wet nail polish;

applying a solvent free silicon based drying accelerator to the wet nail polish;

extracting solvents from the wet nail polish; and drying the nail polish.

10. The method of claim 9 wherein the drying accelerator comprises 25–50% cyclomethicone and 50–75% dimethicone.

* * * * *

UNITED STATES PATENT AND TRADEMARK OFFICE
CERTIFICATE OF CORRECTION

PATENT NO. : 5,549,930
DATED : August 27, 1996
INVENTOR(S) : Moisei Reyzis

It is certified that error appears in the above-indentified patent and that said Letters Patent is hereby corrected as shown below:

On the title page, Item [19] & [76],
Please delete "Reysis" and insert therefor --Reyzis--
Please delete "Moisei Reysis" and insert therefor --Moisei Reyzis--

Signed and Sealed this

Nineteenth Day of May, 1998

Attest:

BRUCE LEHMAN

Attesting Officer     Commissioner of Patents and Trademarks